(12) United States Patent
Garibaldi

(10) Patent No.: US 6,524,303 B1
(45) Date of Patent: Feb. 25, 2003

(54) VARIABLE STIFFNESS MAGNETIC CATHETER

(75) Inventor: Jeffrey M. Garibaldi, St. Louis, MO (US)

(73) Assignee: Stereotaxis, Inc., St. Louis, MO (US)

( * ) Notice: Subject to any disclaimer, the term of this patent is extended or adjusted under 35 U.S.C. 154(b) by 0 days.

(21) Appl. No.: 09/658,368

(22) Filed: Sep. 8, 2000

(51) Int. Cl.$^7$ .............................................. A61M 25/00
(52) U.S. Cl. ........................ 604/525; 600/12; 600/374
(58) Field of Search ................................ 694/525, 523, 694/524, 526, 528, 264; 600/432, 435, 12, 434, 374; 606/170

(56) References Cited

U.S. PATENT DOCUMENTS

| | | |
|---|---|---|
| 3,674,014 A | 7/1972 | Tillander |
| 4,249,536 A | 2/1981 | Vega |
| 4,739,768 A | 4/1988 | Engelson |
| 5,308,342 A | 5/1994 | Sepetka et al. |
| 5,336,205 A | 8/1994 | Zenzen et al. |
| 5,542,938 A | 8/1996 | Avellanet et al. |
| 5,851,185 A * | 12/1998 | Berns .......................... 600/434 |
| 6,375,606 B1 * | 4/2002 | Garibaldi ...................... 600/12 |
| 6,385,472 B1 * | 5/2002 | Hall et al. .................... 600/374 |
| 2002/0029056 A1 * | 3/2002 | Hall et al. .................... 606/170 |

FOREIGN PATENT DOCUMENTS

EP    0422689 A2    4/1991

* cited by examiner

*Primary Examiner*—Teresa Walberg
*Assistant Examiner*—Quang T Van
(74) *Attorney, Agent, or Firm*—Harness, Dickey & Pierce, P.L.C.

(57) ABSTRACT

A steerable magnetic catheter having a proximal end, a distal end, and a lumen therebetween. The catheter has regions of different flexibility along its length. There is a magnetic body adjacent the distal end, which is responsive to an applied magnetic field. The magnetic body is sized and the flexibility of the distal end portion of the catheter is selected so that the distal end of the catheter can be manipulated with a magnetic field of a practical strength, eliminating the need for a guidewire.

3 Claims, 3 Drawing Sheets

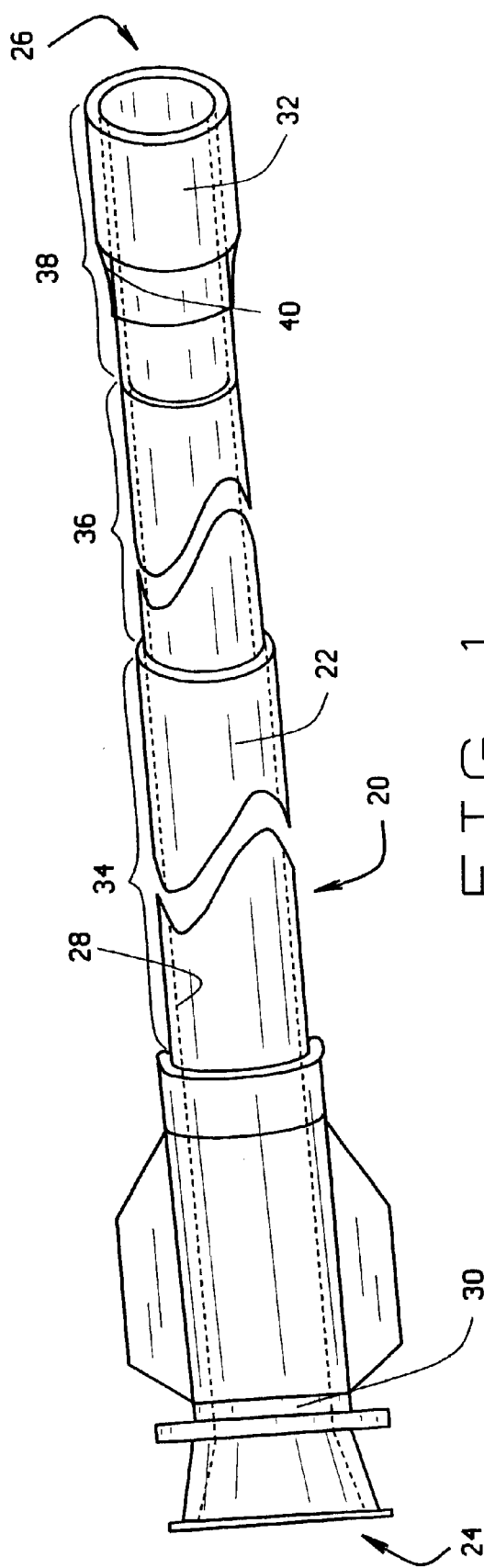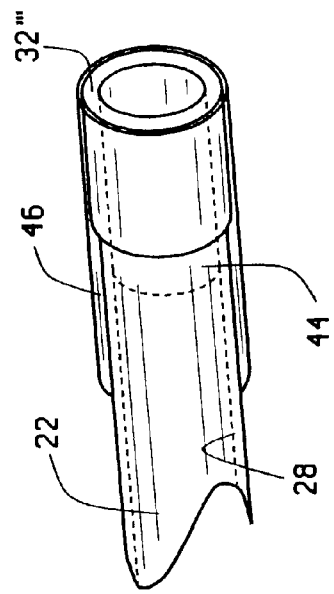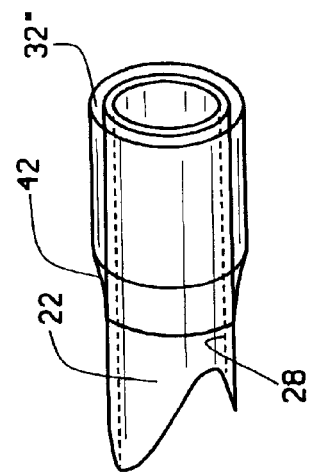

VARIABLE STIFFNESS MAGNETIC CATHETER

FIELD OF THE INVENTION

This invention relates to catheters, and in particular to variable stiffness magnetic catheters.

BACKGROUND OF THE INVENTION

Magnetic catheters are catheters provided with a magnetic member by which the distal end of the catheter can be navigated (oriented and/or moved) by the application of a magnetic field. There are competing considerations in the construction of these catheters. The distal end must be sufficiently flexible to readily orient in response to the force applied by the magnetic field on the magnetic member while the lumen of the distal end must be sufficiently strong to resist kinking. However, the entire catheter must be sufficiently stiff to enable advancement through the patient's body.

SUMMARY OF THE INVENTION

The present invention comprises a steerable magnetic catheter in which the flexibility varies along its length, and which preferably can be navigated without a guidewire. Generally, the catheter has a proximal end and a distal end, and a lumen extending therebetween. The catheter has regions of different flexibility along its length. There is a body, responsive to an applied magnetic field, and/or gradient, adjacent the distal end. The magnetic field and/or gradient may be applied with at least one stationary or at least one moveable magnet.

The body may be a permeable magnetic material, such as cold rolled steel or a permanent magnetic material such as neodymium-iron boron.

The distal end of the catheter is sufficiently flexible and the body is sized such that the catheter can bend at least 45° in response to an applied field of 0.25T or less and more preferably at least 60°, and most preferably 90° within about 5 mm of the magnetic member, which is typically at the distal end of the catheter. This allows navigation in small (less than 5 mm in diameter) vessels. The distal end is more preferably responsive to an applied magnetic field of 0.2T or less, and most preferably to an applied magnetic field of 0.1T or less.

As described above the catheter has at least two, and preferably at least three, regions of different flexibility. Each region is preferably of successively greater flexibility from the proximal end to the distal end.

BRIEF DESCRIPTION OF THE DRAWINGS

FIG. 1 is a perspective view of a variable stiffness magnetic catheter constructed according to the principles of this invention;

FIG. 2 is a perspective view of a first alternate construction of the distal end of the catheter;

FIG. 3 is a perspective view of a second alternate construction of the distal end of the catheter;

FIG. 4 is a perspective view of a third alternate construction of the distal end of the catheter;

Corresponding reference numerals indicate corresponding parts throughout the several views of the drawings.

DETAILED DESCRIPTION OF THE INVENTION

Figure 5:
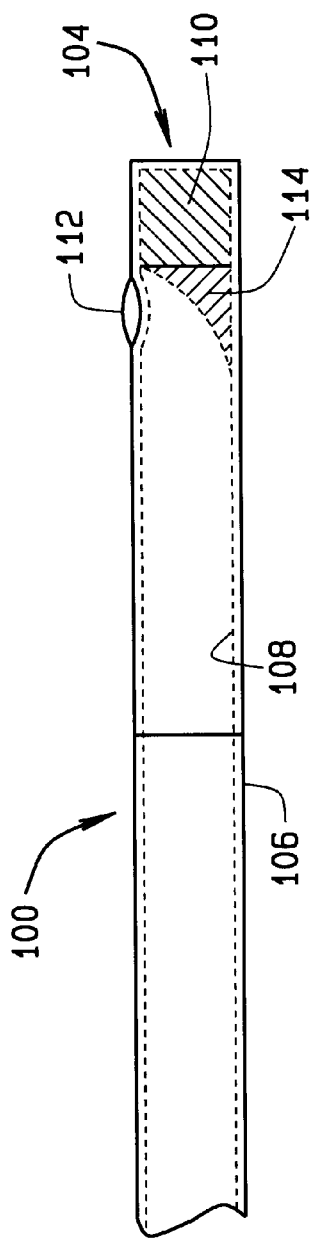
FIG. 5 is a longitudinal cross-sectional view of a second embodiment of a catheter constructed according to the principles of this invention.

A first embodiment of a steerable, variable stiffness magnetic catheter constructed according to the principles of this invention is indicated generally as 20 in FIG. 1. The catheter 20 is a tube 22 having a proximal end 24 and a distal end 26. A lumen 28 extends substantially from the proximal end 24 to the distal end 26.

A conventional luer connector 30 is mounted on the proximal end 24 of the tube 22. A body 32 is mounted on the distal end of the tube 22. The body 32 includes a magnetically responsive material, for example a permeable magnetic material such as cold rolled steel, an iron-cobalt alloy (e.g. 50% iron 50% cobalt) or Hyperco™ or a permanent magnetic material such as neodymium-iron-boron. The body 32 is made of a material, and is of such dimensions, that under the influence of an applied magnetic field, the distal end portion of the catheter aligns with the local applied magnetic field direction. They body may have the form of a solid body, a tube, or a coil.

The tube 22 has regions of different flexibility. In the preferred embodiment shown in FIG. 1, there are three regions 34, 36 and 38. Region 34 has an internal diameter of about 0.021 inches, an outer diameter of about 0.034 inches, and a length of between about 100 cm and about 140 cm. Region 34 is kink-resistant and axially stiff for advancement of the catheter.

Region 36 has an internal diameter of about 0.021 inches, an outer diameter of bout 0.034 inches, and a length of between about 10 cm and about 30 cm. The region 36 preferably has a greater flexibility than region 34. Region 36 is kink-resistant and flexible to allow passage through small vessel branches (i.e., branches less than about 5 mm).

Region 38 has an internal diameter of about 0.021 inches, an outer diameter of about 0.034 inches, and a length of between about 0.5 cm and about 5 cm. The region 38 preferably has a greater flexibility than regions 34 and 36. Region 38 is kink-resistant and extremely flexible to allow magnetic control within small vessel branches (i.e., branches less than about 5 mm).

In the case where catheter 20 is specifically adapted for a neurovascular procedure, the length of the region 34 is selected to extend generally from the patient's femoral artery to the carotid artery; the length of the region 36 is sufficient to pass through the neurovasculature; and the length of the region 38 is sufficient to allow the distal end of the device to align with an applied magnetic field.

Thus the tube flexibility increases from the proximal end to the distal end. The flexibility of each region is preferably constant, but the flexibility of each region could vary along its length so that the increase in flexibility along the length of the catheter is more continuous, with less abrupt changes between adjacent regions.

The body 32 is generally tubular, with an inner diameter of between about 0.022 inches and about 0.026 inches, and an outer diameter of between about 0.033 inches and about 0.038 inches. The body preferably has a volume of about 0.4 mm 3 to about 0.8 mm 3 and a length of between about 1 and about 3 mm. The magnet is sized to be as small as possible, while still providing sufficient torque when a magnetic field is applied to steer the catheter. The body 32 is secured over the region 38 of the tube 22, adjacent the distal end 26, with an adhesive layer or polymer coating 40, which also provides a smooth transition between the body 32 and the external surface of tube 22. The distal-most portion of region 38 has a reduced outside diameter to accommodate the body 32. In this preferred embodiment the outside diameter of the distal region is about 0.023 inches.

A first alternate construction of the distal end is shown in FIG. 2. A generally tubular body 32' is mounted inside the distal end of the tube 22. The body 32' has an inner diameter of about 0.022 inches, and an outer diameter of about 0.032 inches. The body 32' has a length of about 2 mm. The body 32' is frictionally secured inside the lumen 28, and may also be secured with an adhesive layer or polymer coating.

A second alternate construction of the distal end is shown in FIG. 3. A generally tubular body 32" is mounted on the outside of the distal end of the tube 22. The body 32" has an inner diameter of about 0.028 inches, and an outer diameter of about 0.038 inches. The body has a length of about 2 mm. The body 32" can be secured over the region 38 of the tube 22, adjacent the distal end 26, with an adhesive layer or polymer coating 42, which also provides a smooth transition between the body 32" and the external surface of the tube 22. The second alternative construction differs from the primary embodiment in that this second alternate construction the distal most portion of section 38 does not have a reduced outside diameter to accommodate the body 32".

A third alternate construction of the distal end is shown in FIG. 4. A body 32''' is mounted on the distal end of the tube 22 with a collar 44, a portion of which fits inside the lumen 28 of the tube, and a portion of which fits inside the bore of the body 32'''. The collar 44 has an inner diameter of about 0.021 inches, an outer diameter of about 0.022 inches, and a length of about 2.5 mm. The body 32''' has an inner diameter of about 0.023 inches, an outer diameter of about 0.034 inches, and a length of about 1.7 mm. The body 32''' can be secured on the end of the tube 22 with a highly flexible sheath or polymer coating 46 extending over the distal end of the tube and over the body 32'''. The sheath is approximately about 2 mm to about 20 mm long.

Preferably each of the regions 34, 36 and 38 is of successively greater flexibility from the proximal end to the distal end, such that the more distal the region, the more flexible it is. This ensures that the proximal end is sufficiently stiff that the catheter can be advanced by pushing, yet the distal end is sufficiently flexible that applied magnetic field can apply sufficient force to orient and/or move the body. However, a region can be provided with increased stiffness relative to the next most proximal section, for example to improve the ability to advance the catheter.

The body 32 (or 32', 32", or 32''') could comprise a plurality of separate members spaced along the distal end portion of the catheter 20. This allows the shape of the distal end portion to be controlled by the application of an appropriately shaped magnetic field.

The relative length and flexibility of the regions 34, 36 and 38 can be selected to facilitate a particular procedure. For example, the flexible catheter 20 of the preferred embodiment is particularly adapted for interventional neuroradiology procedures, e.g. aneurysm or AVM treatment. The distal-most region 38 is highly flexible and is between about 0.5 cm and about 5 cm long, which is sufficiently long for catheter positioning within vascular defects such as aneurysms. The proximal adjacent region 36 is less flexible and is between about 10 cm and about 30 cm long which is sufficiently long to traverse small vessels within the neurovasculature. Of course different lengths and different flexibilities can be selected to facilitate navigation in other parts of the body.

The outside diameter of the distal end portion of the catheter is preferably less than about 0.038 inches, and more preferably less than about 0.034 inches, so that the distal end of the catheter can fit within small blood vessels, such as those in the brain or at the heart. The inner diameter of the catheter is preferably at least about 0.021 inches, and is smooth and continuous so that objects, such as coils for embolizing aneurysms can be delivered through the lumen.

It is desirable that at least the distal section 38 be flexible enough to permit the distal end to be freely navigated with relatively small applied magnetic fields. It is preferred that at a minimum the catheter can flex at least about 45° under an applied magnetic field of about 0.25T or less, within about 5 mm of the body 32, and more preferably that the catheter can bend at least about 60°, and most preferably at least about 90° with this applied magnetic field. It is of course, even more desirable that the catheter can flex at least about 45° under an applied magnetic field of about 0.2T or less, within about 5 mm of the body, and more preferably at least about 60°, and most preferably at least about 90°. It is most desirable if the catheter can bend at least about 60° under an applied magnet field of about 0.1T or less, within about 5 mm of the body 32, and more preferably that the catheter can bend at least about 60°, and most preferably at least about 90° with this applied magnetic field in this span.

The ability to turn within a 5 mm length of the body has been found sufficient to successfully navigate the neurovasculature and other small vessels between about 1 mm and 5 mm in diameter. Practical magnet systems can generate magnetic fields of up to about 0.25T to about 0.3T in an operating region in a patient. It is preferable to use even lower fields of 0.2T, and preferably as low as 0.1T, to reduce the time required to change the magnetic field direction and thus speed navigation. A 45° bend in the catheter tip is generally sufficient to make 90° turns, and turning is further improved if the catheter can bend at least 60°, and more preferably at least 90°.

While it is desirable that the catheter, and particularly the distal regions of the catheter, be highly flexible, it is important that the catheter not "kink" or bend so sharply that the lumen decreases in size such that it is no longer functional. In general it is desirable that the lumen 28 remain open to the extent that an 0.018 inch diameter coil can pass through the lumen. As described below, coils or braiding can be incorporated into the wall of the catheter to allow flexing while resisting kinking.

The steerable variable stiffness magnetic catheter can be made sufficiently flexible to be flow-directed into blood vessels. Under flow-direction the catheter is sufficiently flexible that the distal end of the catheter will generally follow the branch with the greatest flow. When it is desired to navigate the catheter to a branch other than the branch with the greatest flow, a magnetic field or gradient can be applied to the magnet body 32 on distal end of the catheter 20 to orient and/or move the distal end of the catheter. Thus, the catheter 32 can be used as a magnetically navigable flow-directed catheter.

The distal end of a second embodiment of a steerable variable stiffness magnetic catheter constructed according to the principles of this invention, indicated generally as 100, is shown in a longitudinal cross section in FIG. 5. The catheter 100 comprises at least two sections of different flexibility, and may constructed similar to catheter 20 of the first embodiment.

The catheter 100 has a proximal end (not shown) and a distal end 104, and has a sidewall 106 with a lumen 108 therein extending substantially from the proximal end to the distal end 104. The catheter 100 has a magnet body 110 in its distal end 104. The magnet body 110 may be a permeable magnetic material, such as cold rolled steel, or a permanent magnetic material, such as neodymium-iron boron. Because the magnet body 110 is solid, it has greater mass than the hollow magnet body 32 of the first embodiment, and thus can apply a greater torque to catheter 100 for a given applied magnetic field/gradient than can body 32 on catheter 20.

There is preferably at least one opening 112 in the sidewall 106 of the catheter 100. The size, position and number of openings depends upon the particular application.

Where, for example, the catheter is to be used to deliver coils to embolize an aneurysm, there would be only one opening (to control the placement of the coils), large enough to allow the coils to pass through it. The magnetic moment of the magnetic body could be used to align the side opening, i.e. the magnetic moment can be oriented other than in the axial direction, which would allow the distal end of the catheter to be turned about the axis to align the opening in the sidewall in a particular direction. Where, for example, the catheter is to be used for deploying an elongate medical device, there would also be only one opening through which the device can be deployed. Where, for example, the catheter is used to deliver a medical substance such as a therapeutic agent or a diagnostic agent, there might be a plurality of small openings positioned and arranged around the circumference of the sidewall 106 to deliver the therapeutic or diagnostic agent.

A curved ramp 114 can be provided in the distal end of the lumen 108 to facilitate dispensing coils through the opening 112 and to facilitate deploying medical devices.

Figure 6:
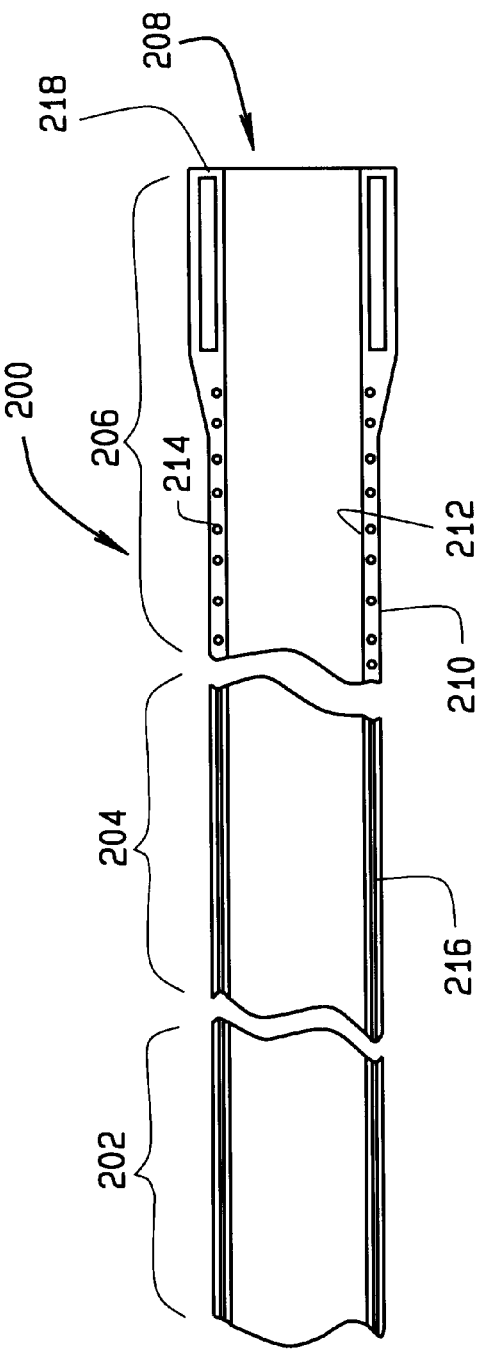
FIG. 6 is a longitudinal cross-sectional view of a third embodiment of a catheter constructed according to the principles of this invention.

The distal end of a third embodiment of a steerable variable stiffness magnetic catheter constructed according to the principles of this invention, indicated generally as 200, is shown in the longitudinal cross section in FIG. 6. The catheter 200 comprises at least two sections of different flexibility, and may be constructed similar to catheter 20. In this preferred embodiment there are three sections, proximal section 202, a more flexible intermediate section 204, and a highly flexible distal section 206.

The catheter 200 has a proximal end (not shown) a distal end 208 with a sidewall 210 with a lumen 212 extending substantially from the proximal end to the distal end 208. There is a tubular magnet 218 embedded in the distal end of the distal section 206, with the bore of the tube aligned with the lumen 212. A wire coil 214 is embedded in the sidewall 210 of the section 206. The coil 214 helps the distal section 206 resist kinking, while leaving the distal section 206 highly flexible. Wire braiding 216 is embedded in the sidewall 210 of the proximal and intermediate sections 202 and 204. The braiding 216 helps stiffen the intermediate and proximal sections 202 and 204 and resist kinking. This construction also helps minimize "ovaling" (i.e., reduction of the cross sectional dimensions) of the inner catheter lumen.

Figure 7:
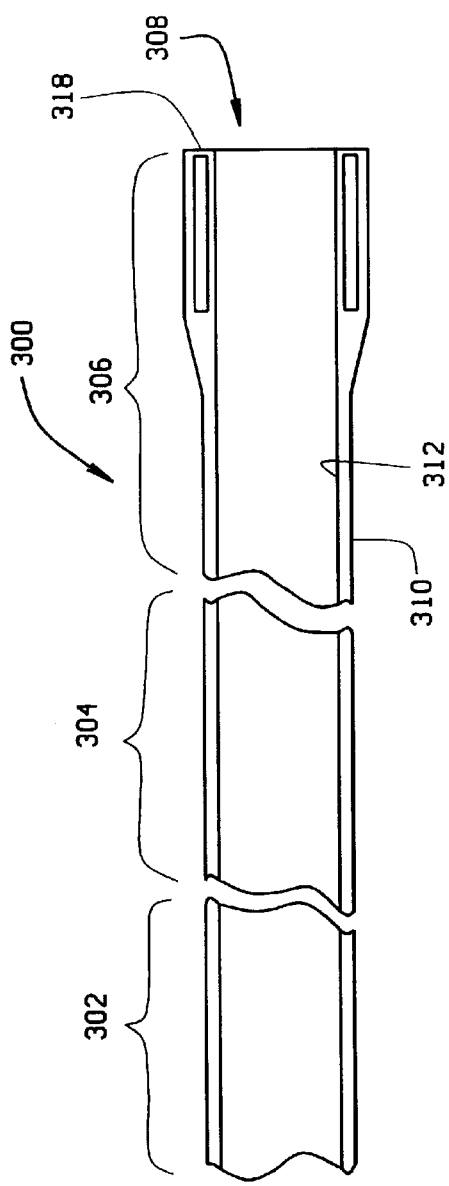
FIG. 7 is a longitudinal cross-sectional view of a fourth embodiment of a catheter constructed according to the principles of this invention.

The distal end of a fourth embodiment of a steerable variable stiffness magnetic catheter constructed according to the principles of this invention, indicated generally 300, is shown in the longitudinal cross section in FIG. 7. The catheter 300 comprises at least two sections of different flexibility, and may be constructed similar to catheter 20. In this preferred embodiment there are three sections, proximal section 302, a more flexible intermediate section 304, and a highly flexible distal section 306. No braiding is employed in this embodiment. Instead, the polymers chosen for the tubing extrusion, separately or in combination, provide the axial and radial support of the catheter, as well as kink resistance, while leaving the distal segment highly flexible.

The catheter 300 has a proximal end (not shown) a distal end 308 with a sidewall 310 with a lumen 312 extending substantially from the proximal end to the distal end 308. There is a tubular magnet 318 embedded in the distal end of the distal section 306, with the bore of the tube aligned with the lumen 312. This construction also helps minimize "ovaling" (i.e., reduction of the cross sectional dimensions) of the inner catheter lumen.

Figure 8:
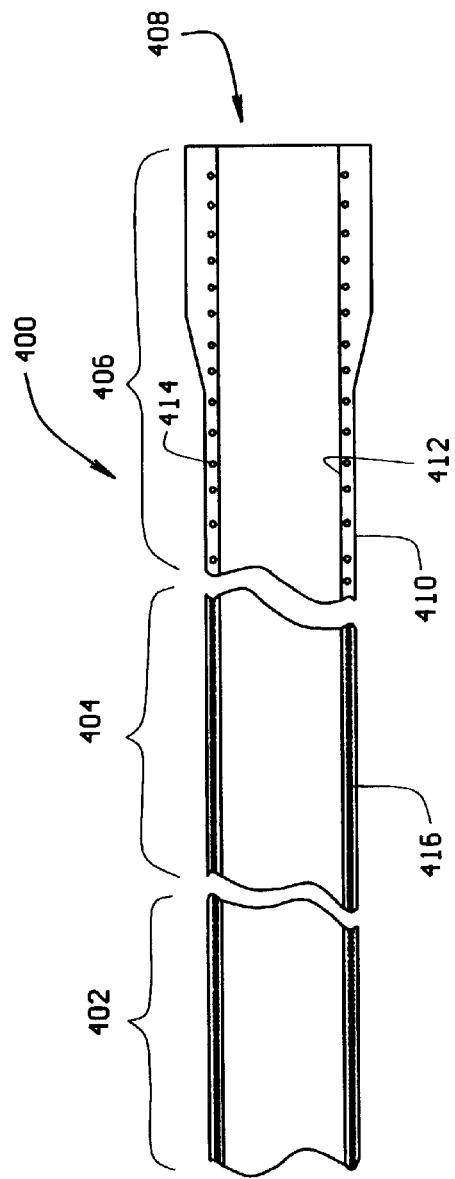
FIG. 8 is a longitudinal cross-sectional view of a fifth embodiment of a catheter constructed according to the principles of this invention.

The distal end of a fifth embodiment of a steerable variable stiffness magnetic catheter constructed according to the principles of this invention, indicated generally 400, is shown in the longitudinal cross section in FIG. 8. The catheter 400 comprises at least two sections of different flexibility, and may be constructed similar to catheter 20. In this preferred embodiment there are three sections, proximal section 402, a more flexible intermediate section 404, and a highly flexible distal section 406.

The catheter 400 has a proximal end (not shown) a distal end 408 with a sidewall 410 with a lumen 412 extending substantially from the proximal end to the distal end 408. A wire coil 414 made from a paramagnetic material such as Hyperco, is embedded in the sidewall 410 of the section 406. Tightly wound (i.e. tight pitch), the distal coil 414 helps the distal section 406 resist kinking, while leaving the distal section 406 highly flexible. When the distal coil is of a more open design (i.e. open pitch), the distal tip 406 becomes magnetically steerable. The magnetic moment of the paramagnetic body could be used to align the side opening, i.e. the magnetic moment can be oriented other than in the axial direction when the coiling pitch is "open", which would allow the distal end of the catheter to be turned about the axis to align the opening in the sidewall in a particular direction. Where, for example, the catheter is to be used for deploying an elongate medical device, there would also be only one opening through which the device can be deployed. Where, for example, the catheter is used to deliver a medical substance such as a therapeutic agent or a diagnostic agent, there might be a plurality of small openings positioned and arranged around the circumference of the sidewall 106 to deliver the therapeutic or diagnostic agent. A non-paramagnetic wire braiding 416 is embedded in the sidewall 410 of the proximal and intermediate sections 402 and 404. The braiding 416 helps stiffen the intermediate and proximal sections 402 and 404 and resist kinking. This construction also helps minimize "ovaling" (i.e., reduction of the cross sectional dimensions) of the inner catheter lumen.

A localization component could be included in the distal end of the catheter, preferably adjacent the magnetic body, to enable non-fluoroscopic localization of the catheter. Such a component might be a magnetic, ultrasonic, or rf localization device. This is particularly useful with side exit catheter

What is claimed is:

1. A method of navigating the distal end of a variable stiffness through branched blood vessel, the method comprising advancing the distal end of the catheter through the blood vessel; selectively allowing the distal end of the catheter to follow the branch having the greatest flow therein; and selectively applying a magnetic field and/or gradient to a magnet body on the distal end of the catheter to move the distal end of the catheter to follow a branch other than the branch having the greatest flow therein.

2. The method according to claim 1 the step of selectively applying a magnetic field and/or gradient is performed with at least one moveable magnet.

3. The method according to claim 1 wherein the step of selectively applying a magnetic field and/or gradient is performed with at least one stationary magnet.

\* \* \* \* \*